US012382570B2

(12) United States Patent
Hae et al.

(10) Patent No.: US 12,382,570 B2
(45) Date of Patent: Aug. 5, 2025

(54) ROTATING CAPACITOR, CIRCULAR ACCELERATOR, AND PARTICLE THERAPY SYSTEM

(71) Applicant: Hitachi High-Tech Corporation, Tokyo (JP)

(72) Inventors: Takamitsu Hae, Tokyo (JP); Masahiro Ikeda, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 438 days.

(21) Appl. No.: 17/902,066

(22) Filed: Sep. 2, 2022

(65) Prior Publication Data

US 2023/0074582 A1    Mar. 9, 2023

(30) Foreign Application Priority Data

Sep. 9, 2021   (JP) .................................. 2021-147099

(51) Int. Cl.
*H05H 7/02* (2006.01)
*A61N 5/10* (2006.01)
*H05H 7/10* (2006.01)
*H05H 13/02* (2006.01)

(52) U.S. Cl.
CPC ............. *H05H 7/02* (2013.01); *A61N 5/1078* (2013.01); *H05H 7/10* (2013.01); *A61N 2005/1087* (2013.01); *H05H 2007/025* (2013.01); *H05H 13/02* (2013.01); *H05H 2277/11* (2013.01)

(58) Field of Classification Search
CPC ............ H05H 7/02; H05H 7/10; H05H 13/02; H05H 2007/025; H05H 2277/11; A61N 5/1078; A61N 2005/1087
See application file for complete search history.

(56) References Cited

U.S. PATENT DOCUMENTS 2,615,129 A     10/1952  McMillan
2014/0103839 A1*  4/2014  Abs ........................ H05H 13/02
                                              315/502

(Continued)

FOREIGN PATENT DOCUMENTS

CN      108684132 A     10/2018
CN      108834301 A     11/2018
JP      09-219342 A      8/1997

(Continued)

OTHER PUBLICATIONS

Extended European Search Report received in corresponding European Application No. 22193805.3 dated Jan. 20, 2023.

(Continued)

*Primary Examiner* — Nicole M Ippolito
(74) *Attorney, Agent, or Firm* — MATTINGLY & MALUR, PC

(57) ABSTRACT

A rotating capacitor is used in a circular accelerator that accelerates a charged particle beam by feeding a first radio frequency to a DC main magnetic field. The rotating capacitor modulates a frequency of the first radio frequency. The rotating capacitor includes a stator electrode and a rotor electrode used for modulating the frequency of the first radio frequency together with the stator electrode. A vacuum seal performs vacuum sealing around a shaft for rotating the rotor electrode. A bearing that supports the shaft is installed on an atmosphere side.

7 Claims, 10 Drawing Sheets

(56) References Cited

U.S. PATENT DOCUMENTS

2016/0093445 A1  3/2016  Mildner et al.
2021/0195725 A1  6/2021  Hae et al.

FOREIGN PATENT DOCUMENTS

| JP | 2015-053513 A | 3/2015 | |
|---|---|---|---|
| JP | 2016-522995 A | 8/2016 | |
| JP | 2019-133745 A | 8/2019 | |
| JP | 2020-095772 A | 6/2020 | |
| WO | WO-201880202 A1 * | 5/2018 | |
| WO | WO-2018180202 A1 * | 10/2018 | ............... H01G 5/01 |
| WO | 2021/002043 A1 | 1/2021 | |

OTHER PUBLICATIONS

Schneider, R. et al., "Nevis Synchrocyclotron Conversion Program—RF System", Proceedings of the 1971 PAC Conference, Jun. 1969, pp. 303-306.

Japanese Office Action received in corresponding Japanese Application No. 2021-147099 dated Jul. 23, 2024.

* cited by examiner

ROTATING CAPACITOR, CIRCULAR ACCELERATOR, AND PARTICLE THERAPY SYSTEM

CROSS-REFERENCE TO RELATED APPLICATION

The present application claims priority from Japanese application JP2021-147099, filed on Sep. 9, 2021, the contents of which is hereby incorporated by reference into this application.

BACKGROUND OF THE INVENTION

1. Field of the Invention

The present invention relates to a rotating capacitor used for a circular accelerator of a particle beam, a circular accelerator, and a particle therapy system using the circular accelerator.

2. Description of the Related Art

A synchrocyclotron and an eccentric orbit type accelerator disclosed in JP 2019-133745 A are known as a circular accelerator of a type in which a main magnetic field intensity is set to be temporally constant and a frequency of an acceleration radiofrequency is temporally modulated. In such circular accelerators, it is relatively easy to making the high magnetic field by using the superconducting coil for generating the main magnetic field. Thus, it is possible to reduce the cost by reducing the size of the accelerator. Therefore, the circular accelerators are particularly applied to a particle therapy system.

In the synchronous cyclotron or the eccentric orbit type accelerator, a rotating capacitor is used as an element that modulates a frequency of a radio frequency for accelerating a charged particle beam. The rotating capacitor generally includes a stator electrode, a rotor electrode disposed to face the stator electrode, a rotation shaft that rotates the rotor electrode, and a bearing that supports the rotation shaft. JP 2020-095772 A discloses an example of such a rotating capacitor.

SUMMARY OF THE INVENTION

The bearing of the rotating capacitor needs to withstand high-speed rotation of the rotation shaft. In addition, a radio-frequency current may flow through the bearing along the wall surface of a housing. Therefore, the bearing is a consumable item, and it is necessary to periodically replace the bearing.

In the rotating capacitor according to the conventional technique, the stator electrode, the rotor electrode, the rotation shaft, and the bearing are disposed in a vacuumed housing. When the bearing is disposed in the vacuumed housing, it is necessary to open the housing to the atmosphere every time the bearing is replaced. In addition, it is necessary to perform the work of opening the housing to the atmosphere, replacing the bearing, and then vacuuming the inside of the housing again. Thus, workability of maintenance of the bearing is deteriorated.

An object of the present invention is to improve workability of maintenance of a bearing of a rotating capacitor used in a circular accelerator.

According to an aspect of the present invention, there is provided a rotating capacitor used in a circular accelerator that accelerates a charged particle beam by feeding a first radio frequency to a DC main magnetic field, the rotating capacitor modulating a frequency of the first radio frequency. The rotating capacitor includes a stator electrode, a rotor electrode that is disposed to face the stator electrode and is used for modulating the frequency of the first radio frequency together with the stator electrode, a vacuum seal that performs vacuum sealing around a rotation shaft for rotating the rotor electrode, and a bearing that is installed on an atmosphere side and supports the rotation shaft.

According to another aspect of the present invention, there is provided a circular accelerator including the rotating capacitor. The charged particle beam is accelerated by feeding the first radio frequency to the DC main magnetic field.

According to still another aspect of the present invention, there is provided a particle therapy system including the circular accelerator, and an irradiation device that irradiates a patient with a charged particle beam extracted from the circular accelerator.

According to the present invention, it is possible to improve workability of maintenance of a bearing of a rotating capacitor used in a circular accelerator.

DESCRIPTION OF THE PREFERRED EMBODIMENTS

Hereinafter, an embodiment of the present invention will be described. The following embodiment is merely an example, and the present invention is not limited to the following specific aspects. The present invention itself can be modified into various forms other than the following embodiment.

Further, a rotating capacitor according to the present invention is suitable for a circular accelerator, but is not limited to the application thereof. The circular accelerator according to the present invention is suitable for a particle therapy system, but is not limited to the application thereof.

Figure 1:
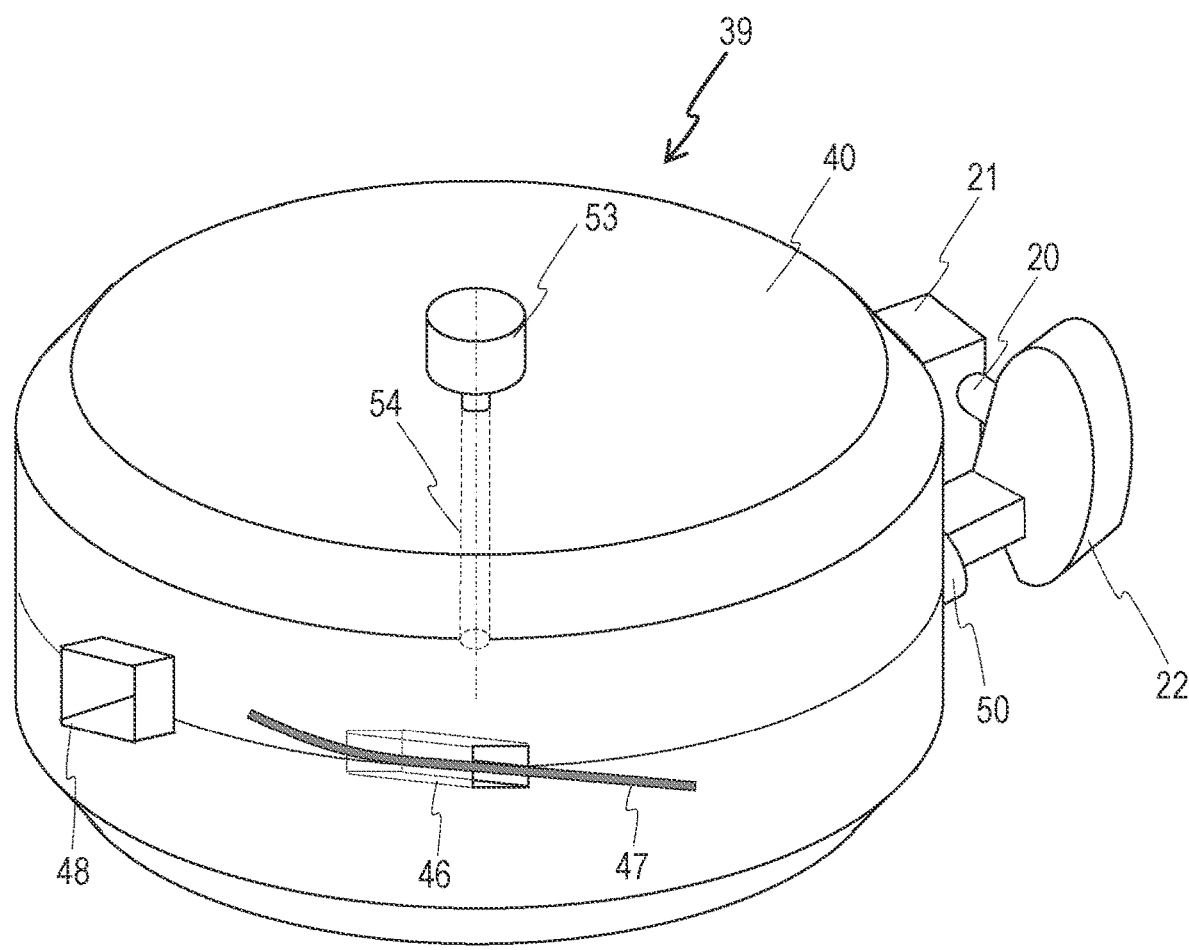
FIG. 1 is a perspective view illustrating an appearance of a circular accelerator according to the present embodiment.
Figure 2:
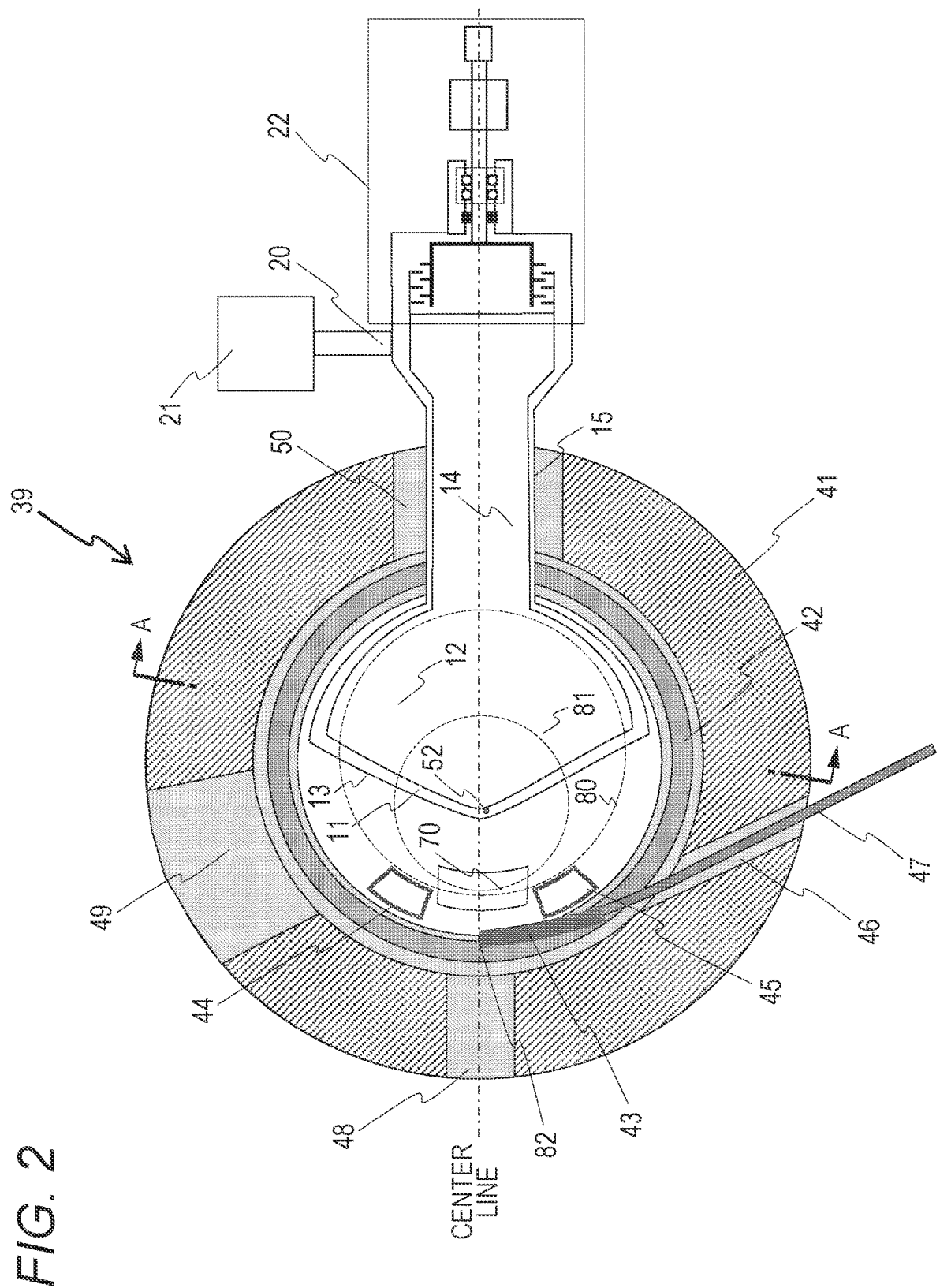
FIG. 2 is a cross-sectional view illustrating the circular accelerator according to the present embodiment.
Figure 3:
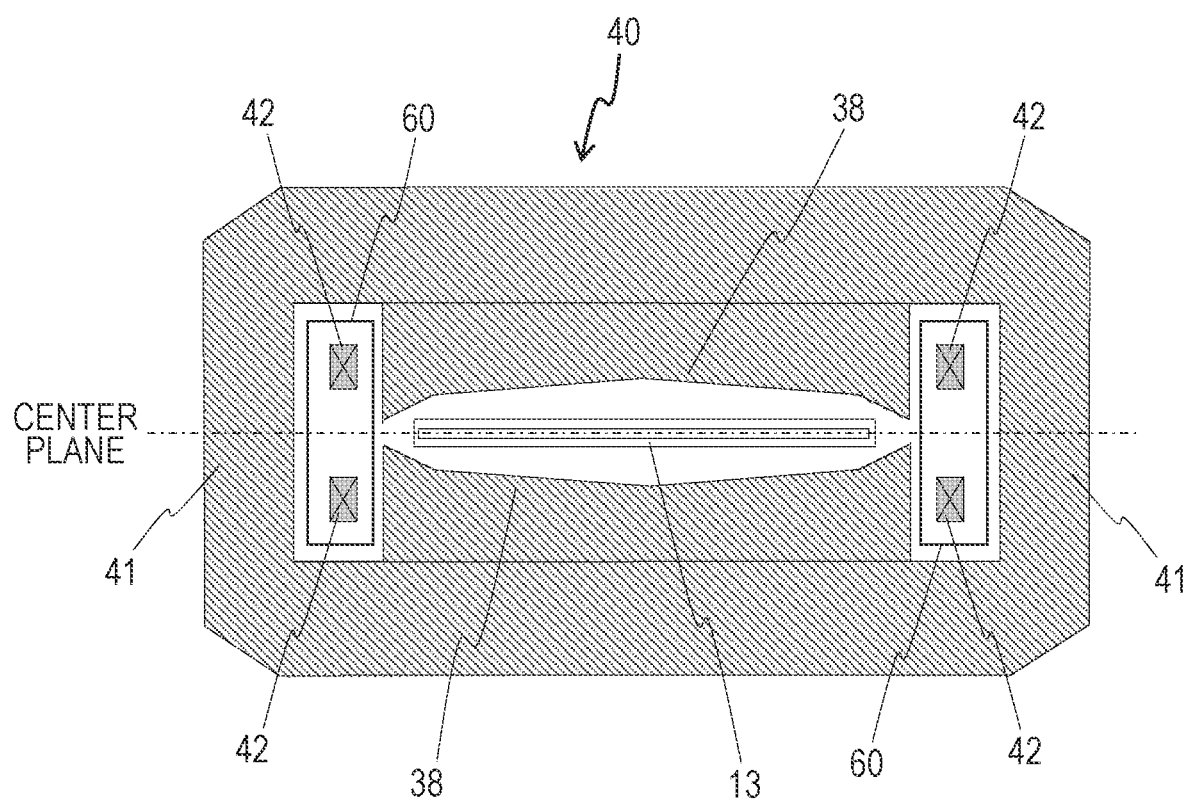
FIG. 3 is a cross-sectional view taken along line A-A in FIG. 2.

A configuration of the circular accelerator according to the present embodiment will be described with reference to FIGS. 1 to 3. FIG. 1 is a perspective view illustrating an appearance of a circular accelerator 39 according to the present embodiment. FIG. 2 is a cross-sectional view illustrating a lateral cross section (center plane) of the circular accelerator 39. FIG. 3 is a cross-sectional view taken along line A-A in FIG. 2, and is a cross-sectional view illustrating a longitudinal cross section of the circular accelerator 39.

The circular accelerator 39 is a device that accelerates a beam by a frequency-modulated radio-frequency electric field in a main magnetic field having temporally constant intensity. As an example, a circular accelerator that accelerates a proton beam to 235 MeV will be described, but the circular accelerator 39 may be a device that accelerates a heavy particle beam of helium, carbon, or the like.

The circular accelerator 39 is an eccentric orbit type accelerator in which a main magnetic field is formed to cause a beam orbit to be eccentric toward a beam extraction path inlet 82. The circular accelerator 39 can extract a beam by freely changing the beam energy between 70 MeV and 235 MeV.

As illustrated in FIGS. 1 and 3, the outer shell of the circular accelerator 39 is formed by a main electromagnet 40 that can be divided in an up-down direction. An acceleration region is formed on the center plane in the main electromagnet 40, and the acceleration region is vacuumed. An orbit through which a beam passes until the energy of the beam reaches 235 MeV of the maximum energy after the beam starts to be accelerated in the acceleration region is referred to as a closed orbit below. Among the closed orbits, an orbit through which a beam having energy of 235 MeV being the maximum energy passes is referred to as a maximum energy orbit 80 (see FIG. 2). An orbit through which a beam having an energy of 70 MeV passes is referred to as a minimum extraction energy orbit. A plane on which the closed orbit draws a spiral is referred to as an orbital plane. A two-dimensional polar coordinate system of the orbital plane, in which the center of the acceleration region is set as an origin, is determined, and an axis in a radially outer direction from the center is referred to as an r-axis.

As illustrated in FIG. 3, the main electromagnet 40 includes a main magnetic pole 38, a yoke 41, and a main coil 42. The appearance of the main electromagnet 40 is formed by the yoke 41. A substantially cylindrical region is formed in the yoke 41. The main coil 42 is an annular superconducting coil and is installed along the inner wall of the yoke 41. A cryostat 60 is installed around the main coil 42, and the main coil 42 is cooled by the cryostat 60. The main magnetic poles 38 are installed on the inner peripheral side of the main coil 42 to vertically face each other. A magnetic field in the up-down direction, which is excited by causing a current to flow in the main coil 42 and is formed by the main magnetic pole 38, is referred to as the main magnetic field. The main magnetic field is used for forming an eccentric orbit. The acceleration region is a region for accelerating a beam in the main magnetic field.

As illustrated in FIG. 2, a plurality of through-holes are formed in the yoke 41. Specifically, a beam through-hole 46, a coil through-hole 48, a vacuuming through-hole 49, and a through-hole for RF accelerating system 50 are formed. The beam through-hole 46 is a through-hole for extracting an accelerated beam. The coil through-hole 48 is a through-hole for drawing out various coil conductors installed in the yoke 41. The vacuuming through-hole 49 is a through-hole for vacuuming the acceleration region. The through-hole for RF accelerating system 50 is a through-hole for an accelerating cavity 10, and is provided on a connection surface between upper and lower magnetic poles.

As illustrated in FIG. 1, an ion source 53 is installed over the main electromagnet 40. The ion source 53 generates a beam of ions injected to the main electromagnet 40. The beam generated by the ion source 53 passes through a low energy beam transport 54 and is injected to the acceleration region in the main electromagnet 40 via an ion injection portion 52. As the ion source 53, an ECR ion source or the like can be applied. The ion source 53 may be disposed inside the vacuumed acceleration region in the main electromagnet 40. In this case, a PIG type ion source or the like is suitable.

As illustrated in FIG. 2, the ion injection portion 52 is disposed closer to the beam extraction path inlet 82 side than the mechanical center of the acceleration region on the center line. A beam of charged particles generated by the ion source 53 passes through the low energy beam transport 54 and is injected to the acceleration region in the main electromagnet 40 by an inflector electrode (not illustrated) or the like via the ion injection portion 52. The injected beam is accelerated by a radio-frequency electric field and circulates in the main magnetic field while increasing energy. As the beam is accelerated, the radius of curvature of the orbit increases, and the beam draws a spiral orbit from the center toward the outside of the acceleration region. The radio frequency for accelerating the beam corresponds to an example of a first radio frequency.

The accelerating cavity 10 is a $\lambda/2$ resonance type cavity and includes a dee electrode 12, a dummy dee electrode 13, an inner conductor 14, an outer conductor 15, and a rotating capacitor 22. The dee electrode 12 is a hollow electrode through which a beam passes, and is joined to the inner conductor 14. The dummy dee electrode 13 is an electrode having a ground potential and is joined to the outer conductor 15 wrapping the inner conductor 14. An acceleration gap 11 is formed between the dee electrode 12 and the dummy dee electrode 13. A radio-frequency electric field is formed in the acceleration gap 11.

The radiofrequency power is supplied to the accelerating cavity 10 by a radiofrequency power supply 21 via an input coupler 20. The input coupler 20 is coupled with the accelerating cavity 10 by either electrostatic coupling or magnetic coupling. Thus, a radio-frequency acceleration voltage for accelerating a beam and a radio-frequency electric field by the radio-frequency acceleration voltage are generated in the acceleration gap 11.

The rotating capacitor 22 is a device for modulating the resonance frequency of the accelerating cavity 10. The resonance frequency of the accelerating cavity 10 is changed by temporally changing the capacitance of the rotating capacitor 22, and thereby a frequency modulation pattern can be formed. An acceleration voltage frequency-modulated by the rotating capacitor 22 is generated in the acceleration gap 11 between the dee electrode 12 and the dummy dee electrode 13. The acceleration gap 11 illustrated in FIG. 2 is an acceleration gap having a harmonic number of 1, that is, an acceleration gap in which the circulating frequency and the acceleration frequency are equal to each other. Such an acceleration gap is formed in accordance with a beam orbit shape.

The radiofrequency power supply 21 supplies radiofrequency power having a frequency that follows a change in the resonance frequency of the accelerating cavity 10, by either a self-excited method or an other-excited system.

The main magnetic field that realizes the eccentric orbit will be described below. The main magnetic field may be a magnetic field of a type in which the main magnetic field intensity is constant in a circumferential direction, or may be an azimuthal varying field (AVF) type magnetic field. For any type of magnetic field, the main magnetic field distribution is a non-isochronous magnetic field. The main magnetic field distribution is determined to satisfy a beam stabilization condition that the n value represented by the following Formula (1) is more than 0 and less than 1.

[Math. 1]

$$n = -\frac{\rho}{|B|}\frac{\partial B}{\partial r} \quad (1)$$

Here, $\rho$ is the deflection radius of a design orbit, B is the magnetic field intensity, and $\partial B/\partial r$ is the magnetic field gradient in a radial direction. Under the above-described beam stabilization condition, a beam slightly deviated in the radial direction from the design orbit receives a restoring force to return to the design orbit, and a beam deviated in a direction perpendicular to the orbital plane receives a restoring force from the main magnetic field in a direction of returning to the orbital plane. That is, the beam performs betatron oscillation in the vicinity of the design orbit, stably circulates, and is accelerated. In the beam of all energies, the betatron frequency (tune in a horizontal direction) $v_r$ in a direction that is parallel to the orbital plane and perpendicular to the orbit is set to a value close to 1. The main magnetic field distribution described above is formed by the main magnetic pole 38 and a trim coil and a magnetic pole piece (both not illustrated) installed on the surface of the main magnetic pole 38. The above components are arranged vertically symmetrically with respect to the orbital plane. Thus, the main magnetic field has only a magnetic field component in a direction perpendicular to the orbital plane, on the orbital plane.

Figure 4:
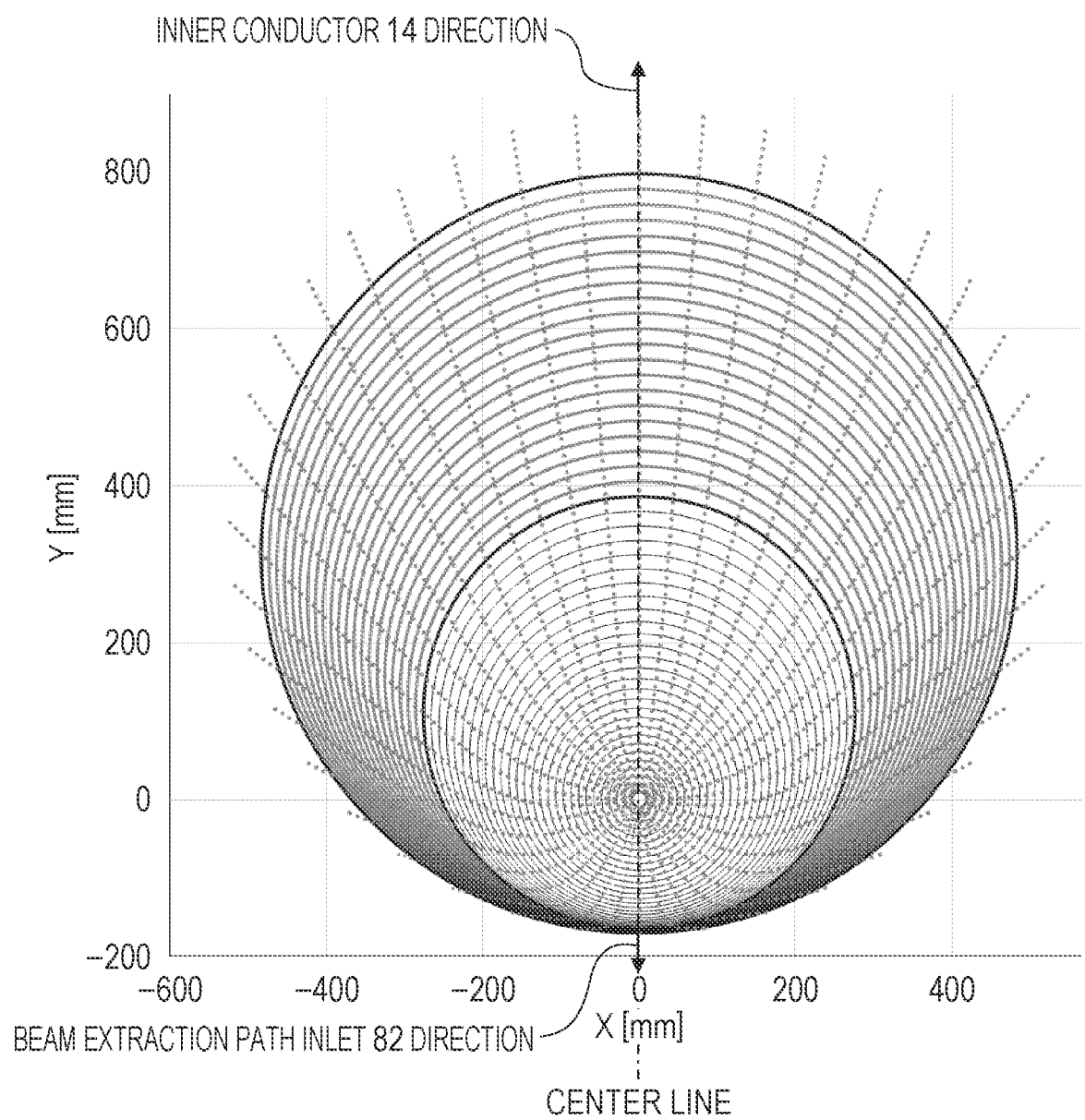
FIG. 4 is a diagram illustrating beam activation for each energy.

FIG. 4 illustrates a closed orbit of each energy. Orbits of 50 kinds of energies are indicated by solid lines for every 0.04 Tm of the magnetic rigidity modulus from the maximum energy of 235 MeV. A dotted line is a line connecting the same circulating phase in each orbit, and is referred to as an equal circulating phase line. The equal circulating phase line is plotted for each circulating phase $\pi/20$ from an aggregation region. The acceleration gap 11 formed between the dee electrode 12 and the dummy dee electrode 13 is installed along the equal circulating phase line. More specifically, the dee electrode 12 has a hollow shape such as a fan shape with a tip near the center of the concentric orbit and a radius along the equal circulating phase line.

An orbit in a region where the energy of the beam is low is close to the concentric orbit centered on the vicinity of the ion injection portion 52, similarly to the conventional cyclotron. The orbits having larger energy are densely gathered on the beam extraction path inlet 82 side. On the other hand, the orbits of the respective energies are in a positional relationship of being spaced from each other on the inner conductor 14 side. A point where the obits are densely gathered is referred to as an aggregation region, and a region where the orbits are discrete is referred to as a discrete region. By forming such orbit arrangement and taking out the beam from the vicinity of the aggregation region, it is possible to reduce a required beam kicking amount. Thus, it is possible to facilitate the beam extraction with variable energy.

Figure 5:
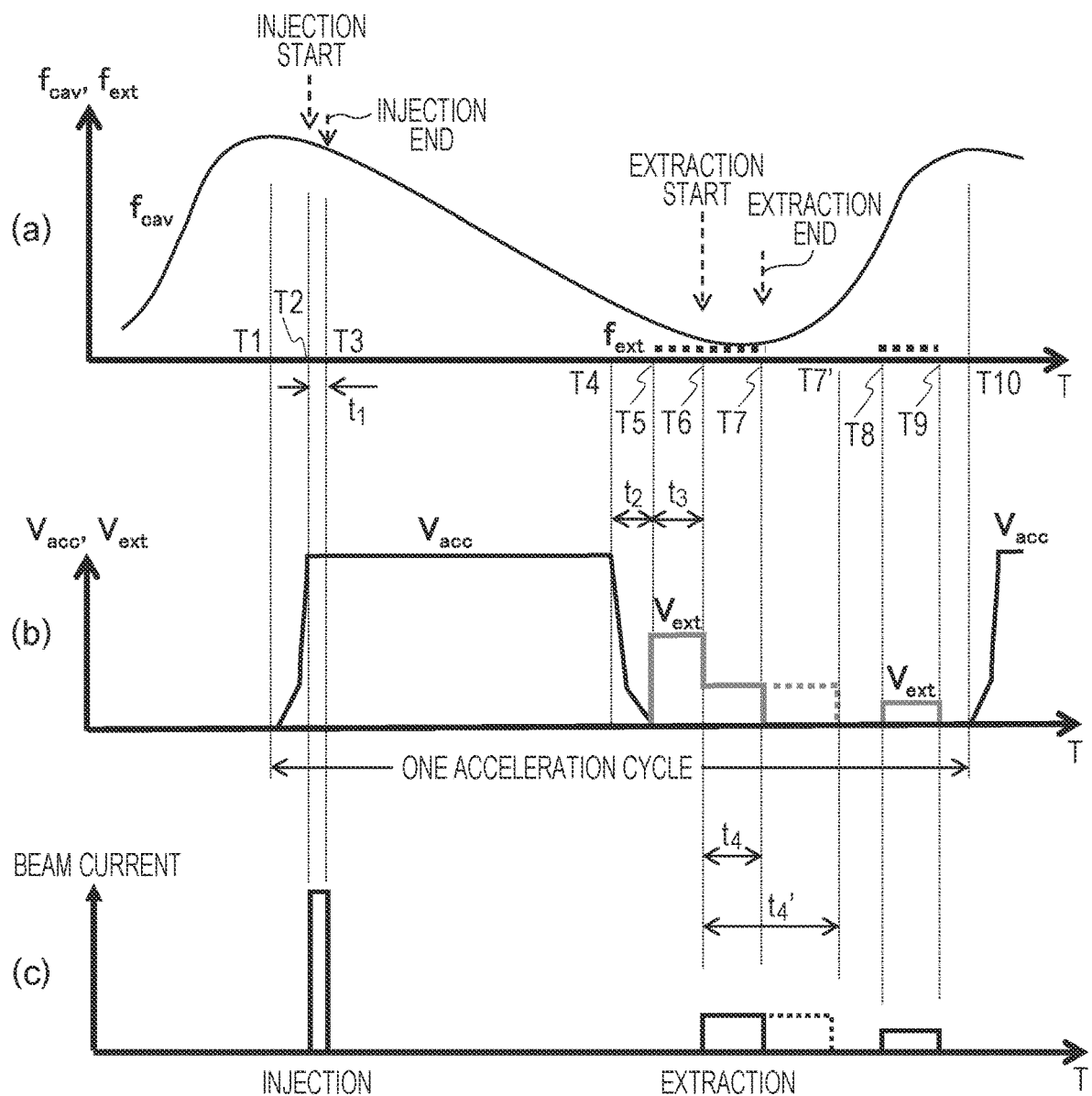
FIG. 5 is a diagram illustrating graphs (a)-(c) of a motion pattern of the circular accelerator according to the present embodiment.

A process until a beam is injected to the circular accelerator 39 and then extracted from the circular accelerator 39 will be described below with reference to the graphs (a)-(c) of FIG. 5. Graph (a) of FIG. 5 illustrates a relationship among the resonance frequency $f_{cav}$ of the accelerating cavity 10, a frequency $f_{ext}$, and the time point T. The frequency $f_{ext}$ is the frequency of the radio-frequency electric field fed to the beam by the radio-frequency kicker 70. Graph (b) of FIG. 5 illustrates a relationship among the acceleration voltage $V_{acc}$ generated in the acceleration gap 11, the radio-frequency voltage $V_{ext}$ fed to the radio-frequency kicker 70, and the time point T. Graph (c) of FIG. 5 illustrates a relationship between the current of the injected beam and the current of the extracted beam, and the time point T. The radio frequency fed to the radio-frequency kicker 70 corresponds to an example of a second radio frequency.

One acceleration cycle starts from the rising edge of the acceleration voltage $V_{acc}$ (time point T1). Then, when the acceleration voltage $V_{acc}$ sufficiently rises, a beam is injected to the circular accelerator 39 from the ion source 53 (time point T2). After a lapse of the time $t_1$ from the injection of the beam to the circular accelerator 39, the radio frequency capturing of the beam ends. The captured beam, that is, the beam ready for acceleration among the injected beams starts to be accelerated by the acceleration voltage $V_{acc}$ (time point T3). When the energy of the beam reaches the energy desired to be taken out, the blocking of the acceleration radio frequency is started (time point T4). When the time $t_2$ elapses, the acceleration voltage $V_{acc}$ is turned off (time point T5), and the beam circulates around a certain orbit. The individual charged particles forming the beam oscillates in a direction perpendicular to the orbit of the beam at the time of circulating. This oscillation is referred to as betatron oscillation, and the frequency of this oscillation is referred to as a betatron frequency. The frequency per round is referred to as a tune, and the displacement on the r-axis of the beam to the outside of the orbit plane per round is referred to as turn separation. Regarding the circulating beam, the betatron oscillation in a direction orthogonal to the orbit of the beam in the orbital plane is referred to as a horizontal betatron oscillation, and the tune is referred to as a horizontal tune. This betatron oscillation has a property that resonance occurs and the amplitude rapidly increases when an appropriate radio-frequency voltage is fed.

When $V_{acc}$ is turned OFF, the feeding of the radio-frequency voltage $V_{ext}$ to the radio-frequency kicker 70 is started. The start of the feeding of the radio-frequency voltage $V_{ext}$ to the radio-frequency kicker 70 (time point T5) does not have to be exactly the same as when the acceleration voltage $V_{acc}$ is turned OFF. The feeding of the radio-frequency voltage $V_{ext}$ may be started immediately before, simultaneously with, or immediately after the start of blocking of the acceleration radio frequency (time point T4), or may be started immediately before or immediately after the acceleration voltage $V_{acc}$ is in the OFF state. The energy desired to be taken out can be controlled by the feeding time of the acceleration voltage $V_{acc}$.

The radio-frequency voltage of the radio-frequency kicker 70 quickly rises with a response of several μs if the radio-frequency kicker 70 does not have a resonator structure and is designed so that the capacitance has an appropriate value. The betatron oscillation have the property that the amplitude increases resonantly when the product of either the horizontal tune or the fractional part of the horizontal tune and the circulating frequency of the beam is substantially equal to the frequency of the fed radio-frequency voltage. Thus, the frequency $f_{ext}$ of the radio-frequency voltage is determined to be substantially same as the product $\Delta v_r \times f_{rev}$ of the fractional part $\Delta v_r$ of the horizontal tune $v_r$ of the maximum energy beam and the circulating frequency $f_{rev}$ of the beam having energy desired to be taken out. Alternatively, a radio-frequency voltage of a finite frequency bandwidth including a frequency component that is substantially the same as the product $\Delta v_r \times f_{rev}$ may be fed. As a result, the amplitude of the horizontal betatron oscillation continues to increase resonantly, and the beam eventually reaches a peeler magnetic field region 44 and a regenerator magnetic field region 45 installed on the outer peripheral side of the maximum energy orbit 80 (time point T6).

The beam that has reached the peeler magnetic field region 44 is kicked to the outer peripheral side of the orbit plane. The beam that has reached the regenerator magnetic field region 45 is kicked to the inner peripheral side of the orbit plane. Kicking refers to deflecting a beam by feeding an electric field or a magnetic field. The quadrupole magnetic field component of the peeler magnetic field region 44 kicks the beam further to the outer peripheral side, and the turn separation increases. At the same time, the magnetic field of the regenerator magnetic field region 45 suppresses an occurrence of a situation in which the horizontal tune of the beam changes abruptly and prevents an occurrence of a situation in which the betatron oscillation diverges in a vertical direction perpendicular to a horizontal direction by 90 degrees before the beam is extracted, thereby preventing the beam from being lost. When the magnetic field intensity of each of the peeler magnetic field region 44 and the regenerator magnetic field region 45 are appropriately adjusted, the resonance condition of the betatron oscillation of $2v_r=2$ can be generated to increase the turn separation.

As illustrated in FIG. 2, a septum coil 43 is installed at the beam extraction path inlet 82. When the turn separation greatly exceeding the thickness of a coil conductor (not illustrated) installed on the inner peripheral side of the septum coil 43 is obtained, the beam is guided into the septum coil 43. The beam is sufficiently deflected, is guided to high energy beam transport 47, and then is extracted.

Immediately after the feeding of the radio-frequency voltage to the radio-frequency kicker 70 is started (time point T5), a radio-frequency voltage as large as possible is fed to quickly increase the amplitude of the beam. Thus, it is possible to reduce the time until the beam extraction. The radio-frequency voltage is decreased immediately before the beam reaches the peeler magnetic field region 44 or the regenerator magnetic field region 45 (time point T6), and the amount of the beam traveling to the peeler magnetic field region 44 and the regenerator magnetic field region 45 is adjusted. In this manner, it is possible to finely control a beam extraction current. It is possible to change the extraction current of the beam by sweeping the frequency of the radio frequency fed to the radio-frequency kicker 70 or changing the phase of the gear radio frequency instead of lowering the radio-frequency voltage $V_{ext}$. This utilizes a property that the betatron frequency of charged particles included in the beam varies with certain distribution (tune spread). It is possible to change the extraction current of the beam by changing the frequency of the radio frequency and changing the band of the distribution of the frequency of the charged particles that cause resonance.

The extraction of the beam is stopped (time point T7) by stopping the feeding of the radio-frequency voltage $V_{ext}$ to the radio-frequency kicker 70 after the time $t_4$ has elapsed from the start of the extraction of the beam (time point T6). It is possible to control the extraction time of the beam by adjusting the time $t_4$.

It is possible to adjust the beam extraction current by controlling the radio-frequency voltage fed to the radio-frequency kicker 70. In addition, it is possible to stop the beam extraction by stopping the application of the radio-frequency voltage. Therefore, the spot dose required for scanning irradiation can be irradiated with one emission pulse beam without excess or deficiency, and the dose rate is improved. For example, as illustrated in FIG. 5, if the radio-frequency voltage $V_{ext}$ is continuously fed to the radio-frequency kicker 70 until the time $t_4'$ elapses from the start of extraction of the beam (time point T6), the beam can be extracted until a time point T7'.

In addition, if a beam circulating in the accelerator remains after extraction, the beam extraction can be resumed by feeding the radio-frequency voltage $V_{ext}$ again (time point T8). Thus, it is possible to use the beam for the next spot irradiation without performing injection, capturing, and acceleration of the beam again. That is, since the beam can be extracted a plurality of times within one acceleration cycle, it is possible to use charges injected from the ion source 53 without waste, and the dose rate is further improved. If the acceleration voltage $V_{acc}$ starts to rise again, a new acceleration cycle starts (time point T10).

The rotating capacitor 22 will be described below in detail with reference to FIG. 6. The rotating capacitor 22 is installed at an end portion of the accelerating cavity 10 opposite to the dee electrode 12. The rotating capacitor 22 includes a motor 31, a stator electrode 32, a rotor electrode 33, a shaft 35 connecting the rotor electrode and the motor 31, a rotary joint 34, a vacuum seal 29, a bearing 30 of the shaft 35, and a holder 28.

The stator electrode 32 is formed on the inner conductor 14. The rotor electrode 33 is adjacent to the outer conductor 15 and is not physically connected to the outer conductor 15, but is electrically connected to the outer conductor 15 via electrostatic capacitance. Contrary to this configuration, the stator electrode 32 may be formed (physically connected) on the outer conductor 15, and the rotor electrode 33 may be electrostatically coupled to the inner conductor 14.

Figure 6:
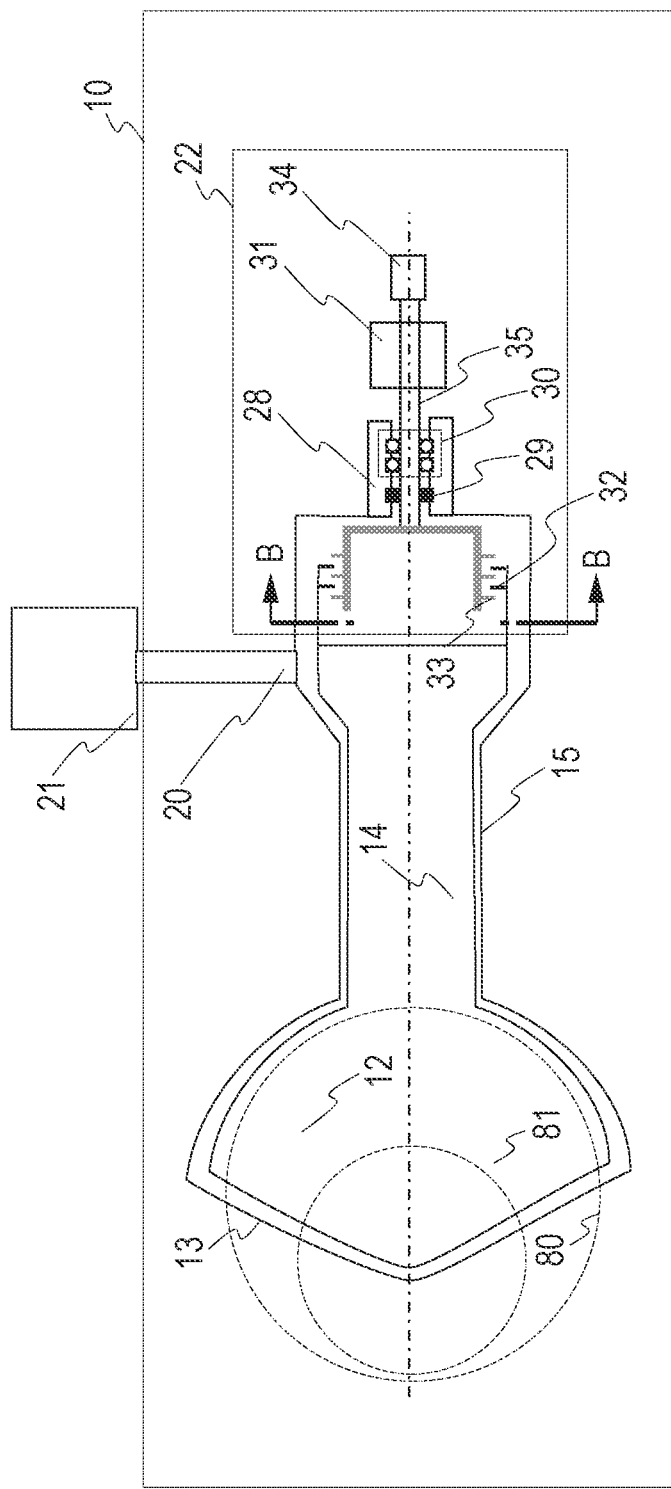
FIG. 6 is a cross-sectional view illustrating an accelerating cavity and a rotating capacitor according to the present embodiment.
Figure 7:
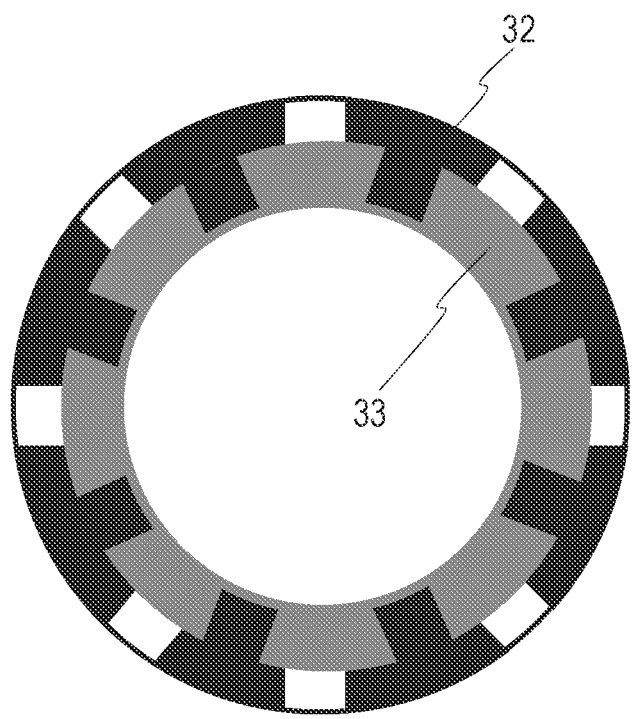
FIG. 7 is a cross-sectional view taken along line B-B in FIG. 6.

FIG. 7 is a cross-sectional view taken along line B-B in FIG. 6. The stator electrode 32 and the rotor electrode 33 have a periodically symmetric structure having a notched portion of a certain shape in the circumferential direction, in order to realize a frequency modulation pattern illustrated in graph (a) of FIG. 5. By changing the area of the facing portion between the stator electrode 32 and the rotor electrode 33, the capacitance formed between the stator electrode 32 and the rotor electrode 33 changes with time.

In the example illustrated in FIG. 7, the periodically symmetric structure is a structure that is symmetrical eight times. Thus, the frequency modulation pattern is repeated for eight cycles every time the motor 31 makes one rotation. If the number of times of periodical symmetry is further increased, it is possible to reduce the motor rotation speed, and it is possible to increase the lifespans of the vacuum seal and the bearing.

The shaft 35 is installed to penetrate the center of the motor 31. The rotary joint 34 is installed at an end portion of the shaft 35, and cooling water is supplied into the shaft 35. The cooling water is used for cooling the rotor electrode 33. The motor 31 illustrated in FIG. 6 is merely an example. The motor used in the rotating capacitor 22 may have a structure other than the structure sharing the shaft and the rotation axis. For example, a motor may be installed beside the shaft, and the shaft may be driven via a gear, a pulley, or the like.

The holder 28 is water-cooled to hold and cool the vacuum seal 29 and the bearing 30. The vacuum seal 29 is installed on the dee electrode 12 side, and vacuum-seals the periphery of the shaft 35. The bearing 30 that supports the shaft 35 is installed on the opposite side of the dee electrode 12. That is, the bearing 30 is installed on the atmosphere side. Since the bearing 30, which is a consumable, is installed on the atmosphere side, maintenance work such as replacement of the bearing 30 is facilitated. In addition, since it is not necessary to open the vacuum for the maintenance work, it is possible to reduce the down time of the circular accelerator 39. Even though the grease used in the bearing 30 generates dust, the place is in the atmosphere and does not cause deterioration of the degree of vacuum. Thus, problems such as discharge and beam loss do not occur.

As the vacuum seal 29, a lip seal, a double O-ring, a Wilson seal, a bellows seal, or the like is used. When the rotation speed of the motor 31 is equal to or less than 2000 rpm, a magnetic fluid seal can be used. This increases the slidability, so that it is possible to expect the increase of the seal lifespan.

The stator electrode 32, the rotor electrode 33, the inner conductor 14, the outer conductor 15, and the shaft 35, which can be paths through which a radio-frequency current flows, are all members made of conductors.

Figure 8:
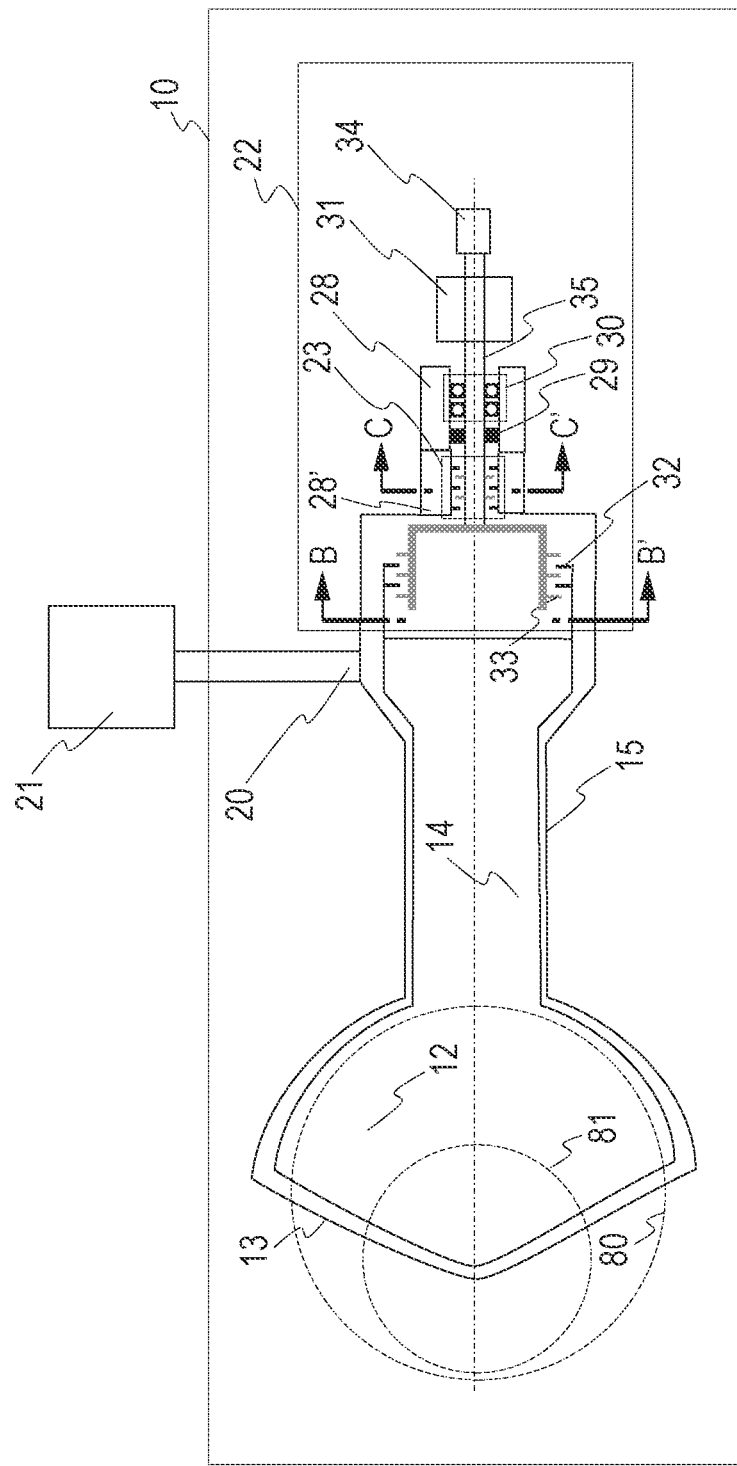
FIG. 8 is a cross-sectional view illustrating a rotating capacitor according to a first modification example.

FIG. 8 illustrates a rotating capacitor according to a first modification example. In order to reduce the radio-frequency current flowing through the vacuum seal 29 and the bearing 30, the bypass capacitor 23 may be installed on the vacuum side of the vacuum seal 29 as illustrated in FIG. 8. The bypass capacitor 23 includes a holder-side electrode 24 and a shaft-side electrode 25 facing each other. The holder-side electrode 24 is an electrode fixed to a holder 28' that is made of a conductor and is connected to the outer conductor 15. The shaft-side electrode 25 is an electrode fixed on the shaft 35.

Figure 9:
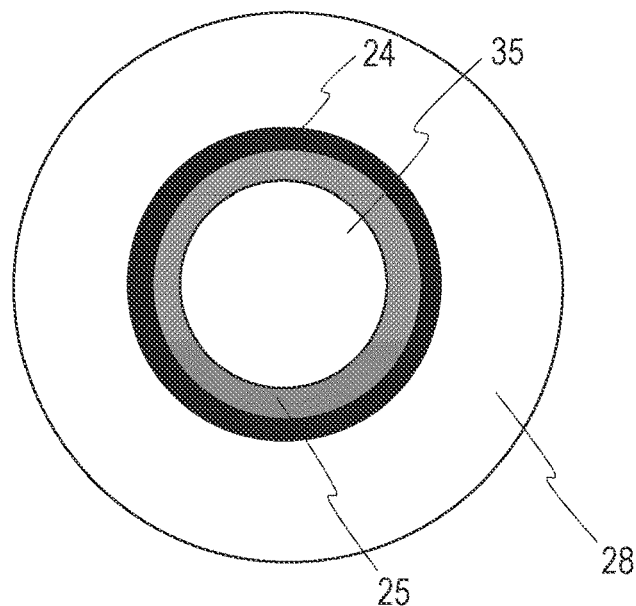
FIG. 9 is a cross-sectional view taken along line C-C in FIG. 8.

FIG. 9 illustrates the configuration of the bypass capacitor 23. FIG. 9 is a cross-sectional view taken along line C-C in FIG. 8. The holder-side electrode 24 and the shaft-side electrode 25 are electrodes having no notched portion in the circumferential direction. With this configuration, the capacitance increases, and the impedance with respect to the radio frequency decreases. Therefore, the radio-frequency current easily flows through the bypass capacitor 23, and the radio-frequency current flowing through the vacuum seal 29 and the bearing 30 is reduced, so that it is possible to improve the lifespans of the vacuum seal 29 and the bearing 30 and reduce the frequency of the maintenance work.

Similar to the stator electrode and the rotor electrode, the holder-side electrode 24 and the shaft-side electrode 25 may have notched portions in the circumferential direction. When there is the notched portion, the capacitance decreases, but a capacitance change contributing to resonance frequency modulation can be caused similar to the stator electrode and the rotor electrode. In addition, the holder-side electrode 24 and the shaft-side electrode 25 are configured to have the same wobbling radius as those of the stator electrode and the rotor electrode, and it is possible to enhance the bypass effect of the radio-frequency current by increasing the capacitance.

When a magnetic fluid seal is used as the vacuum seal 29, the shaft 35 needs to be made of a magnetic material in order to form a magnetic path. If the holder 28 is also made of a magnetic material, it is possible to block a leakage magnetic field leaking from the main electromagnet 40. In addition, a magnetic fluid shield that covers a region from the outer peripheral side of the outer conductor 15 to the outer peripheral side of the holder 28 may be installed, and a magnetic shield structure that blocks a leakage magnetic field including not only the magnetic fluid shield and the bearing 30 but also the rotor electrode 33 may be adopted.

As a result, it is possible to reduce both a decrease in sealing performance of the magnetic fluid seal caused by the leakage magnetic field and an eddy current loss generated in the rotor electrode 33. Furthermore, when the entire rotating capacitor 22 is covered with a housing that is made of a conductor and is connected to the outer conductor 15 without any gap, it is possible to suppress radio-frequency noise that may be diffused from the shaft 35 to the surrounding space.

Figure 10:
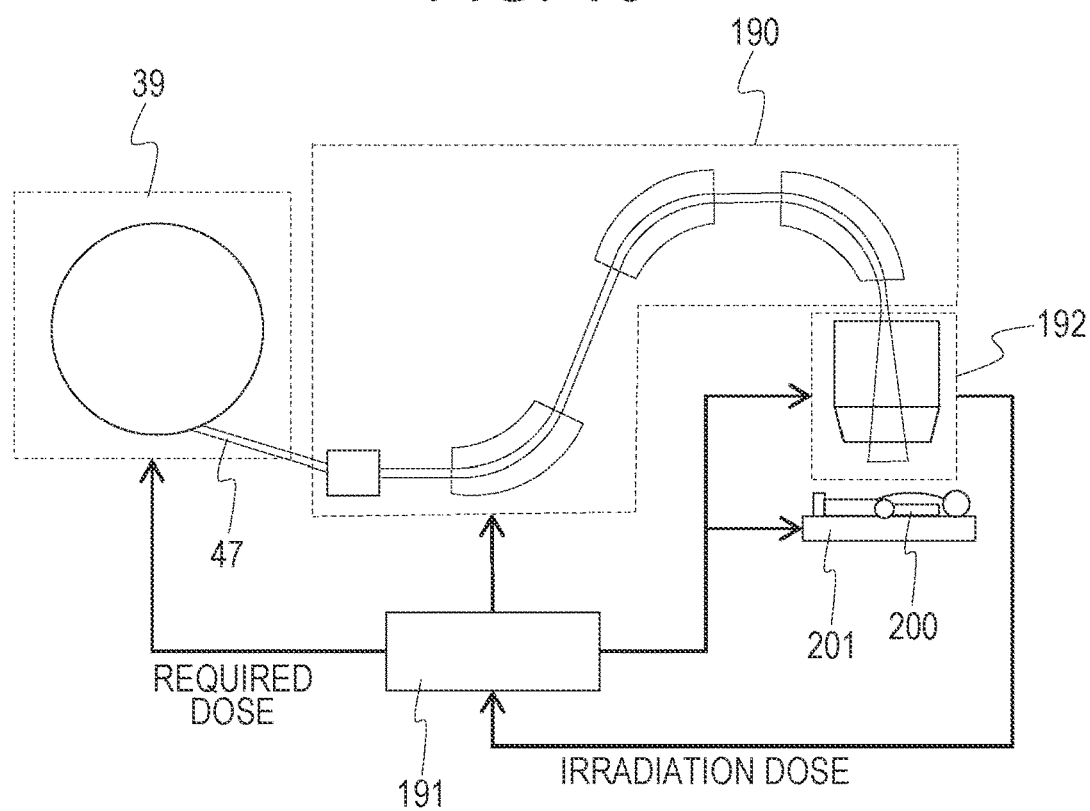
FIG. 10 is a diagram illustrating a configuration of a particle therapy system.

The configuration of a particle therapy system according to the present embodiment will be described below with reference to FIG. 10. FIG. 10 illustrates the configuration of the particle therapy system. The particle therapy system according to the present embodiment includes the circular accelerator 39, a rotating gantry 190, an irradiation device 192 including a scanning coil, a therapy stand 201, and a control apparatus 191 that controls the above components. The beam extracted from the circular accelerator 39 is transported to the irradiation device 192 by the rotating gantry 190. The transported ion beam is shaped to match with the target shape by the irradiation device 192 and the adjustment of the beam energy, and the target of the patient 200 lying on the therapy stand 201 is irradiated by a predetermined amount. The irradiation device 192 includes a dose monitor and monitors the dose with which the patient 200 is irradiated for each irradiation spot. The control apparatus 191 calculates a required dose to each irradiation spot based on the dose data, and outputs the calculation result to an arithmetic operation device.

According to the rotating capacitor 22 of the present embodiment, the bearing 30, which is a consumable item, is installed on the atmosphere side. Thus, it is not necessary to open the circular accelerator 39 to the atmosphere when the maintenance work of the bearing 30 (for example, replacement of the bearing 30) is performed. That is, it is possible to perform the maintenance of the bearing 30 without opening the circular accelerator 39 to the atmosphere. Therefore, it is possible to improve the efficiency of the maintenance work of the bearing 30. In addition, since it is not necessary to open the circular accelerator 39 to the atmosphere, it is possible to reduce the down time of the circular accelerator 39. As a result, it is possible to lengthen the operating time of the particle therapy system using the circular accelerator 39, and improve the throughput of the patient.

Figure 11:
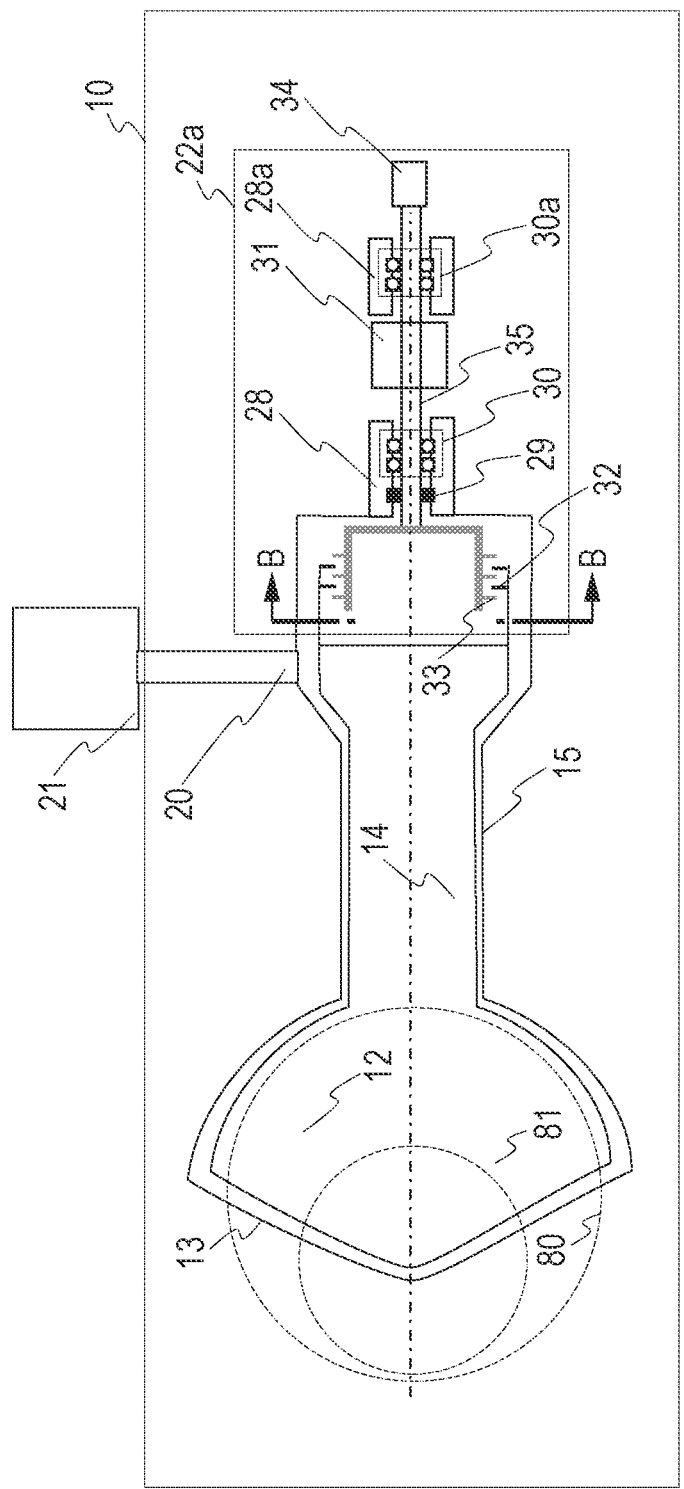
FIG. 11 is a cross-sectional view illustrating a rotating capacitor according to a second modification example.

A rotating capacitor according to a second modification example will be described below with reference to FIG. 11. FIG. 11 is a cross-sectional view illustrating the rotating capacitor according to the second modification example.

A rotating capacitor 22a according to the second modification example further includes a bearing 30a and a holder 28a in addition to the configuration of the rotating capacitor 22 illustrated in FIG. 6. In the second modification example, the bearing 30 corresponds to an example of a first individual bearing, and the bearing 30a corresponds to an example of a second individual bearing. The shaft 35 is supported by the bearings 30 and 30a. The holder 28a holds the bearing 30a. The bearings 30 and 30a are installed at positions spaced from each other on the shaft 35.

When the bearing is installed on the atmosphere side, the shaft 35 is longer than when the bearing is installed on the vacuum side, but the shaft 35 can be stably supported by installing the bearings 30 and 30a at the positions spaced from each other.

Three or more bearings may be installed, and the shaft 35 may be supported by the three or more bearings.

What is claimed is:

1. A rotating capacitor used in a circular accelerator that accelerates a charged particle beam by feeding a first radio frequency to a DC main magnetic field, the rotating capacitor modulating a frequency of the first radio frequency, the rotating capacitor comprising:
   a stator electrode;
   a rotor electrode that is disposed to face the stator electrode and is used for modulating the frequency of the first radio frequency together with the stator electrode;
   a vacuum seal that performs vacuum sealing around a rotation shaft for rotating the rotor electrode; and
   a bearing that is installed on an atmosphere side and supports the rotation shaft.

2. The rotating capacitor according to claim 1, wherein the vacuum seal is a magnetic fluid seal.

3. The rotating capacitor according to claim 1, further comprising a bypass capacitor that is installed between the vacuum seal and the rotor electrode, and includes a counter electrode.

4. The rotating capacitor according to claim 1, wherein
   the bearing includes a first individual bearing and a second individual bearing, and
   the first individual bearing and the second individual bearing are installed at positions spaced from each other on the rotation shaft.

5. A circular accelerator comprising:
   the rotating capacitor according to claim 1, wherein
   the charged particle beam is accelerated by feeding the first radio frequency to the DC main magnetic field.

6. The circular accelerator according to claim 5, further comprising a radio-frequency kicker, wherein
   the charged particle beam is extracted by feeding a second radio frequency to the radio-frequency kicker, the second radio frequency having a frequency different from the frequency of the first radio frequency.

7. A particle therapy system comprising:
   the circular accelerator according to claim 5; and
   an irradiation device that irradiates a patient with a charged particle beam extracted from the circular accelerator.

* * * * *